(12) United States Patent
Matteuzzi

(10) Patent No.: US 9,884,138 B2
(45) Date of Patent: Feb. 6, 2018

(54) FILLER COMPOSITION FOR THE TREATMENT OF LIPOATROPHY

(71) Applicant: ADVANCED AESTHETIC TECHNOLOGIES, INC., Brookline, MA (US)

(72) Inventor: Mauro Matteuzzi, Bologna (IT)

(73) Assignee: Advanced Aesthetic Technologies, Inc., Brookline, MA (US)

( * ) Notice: Subject to any disclaimer, the term of this patent is extended or adjusted under 35 U.S.C. 154(b) by 0 days.

(21) Appl. No.: 15/443,216

(22) Filed: Feb. 27, 2017

(65) Prior Publication Data

US 2017/0165397 A1    Jun. 15, 2017

Related U.S. Application Data

(63) Continuation of application No. 14/782,171, filed as application No. PCT/IB2014/060322 on Mar. 31, 2014, now Pat. No. 9,579,418.

(30) Foreign Application Priority Data

Apr. 4, 2013 (IT) .............. MI2013A0507

(51) Int. Cl.
| | | |
|---|---|---|
| A61K 8/02 | (2006.01) |
| A61L 27/26 | (2006.01) |
| A61K 8/73 | (2006.01) |
| A61L 27/20 | (2006.01) |
| A61L 27/58 | (2006.01) |
| A61Q 19/08 | (2006.01) |
| A61L 27/12 | (2006.01) |
| A61L 27/02 | (2006.01) |
| A61K 8/24 | (2006.01) |
| A61K 8/20 | (2006.01) |

(52) U.S. Cl.
CPC ............ *A61L 27/26* (2013.01); *A61K 8/20* (2013.01); *A61K 8/24* (2013.01); *A61K 8/73* (2013.01); *A61K 8/735* (2013.01); *A61L 27/025* (2013.01); *A61L 27/12* (2013.01); *A61L 27/20* (2013.01); *A61L 27/58* (2013.01); *A61Q 19/08* (2013.01); *A61L 2400/06* (2013.01); *A61L 2430/34* (2013.01)

(58) Field of Classification Search
CPC ........ A61L 27/26; A61L 27/025; A61L 27/12; A61L 27/20; A61L 27/58; A61L 2400/06; A61L 2430/34; A61K 8/20; A61K 8/24; A61K 8/73; A61K 8/735; A61Q 19/08
See application file for complete search history.

(56) References Cited

PUBLICATIONS

Zhang et al (Carbohydrate Polymers, 2012, 88, 1445-1452).*
Shinji et al (JP2006008616, published Jan. 12, 2006, Machine Translation).*

* cited by examiner

Primary Examiner — Kortney L Klinkel
Assistant Examiner — Ibrahim D Bori
(74) Attorney, Agent, or Firm — Brown Rudnick LLP; Thomas C. Meyers

(57) ABSTRACT

The present invention refers to a composition that is useful as a filler for the correction of soft tissue volume loss, for example for the cosmetic treatment of wrinkles, or for the treatment of disorders such as lipoatrophy or lipodystrophy in general, said composition comprising agarose and hyaluronic acid, or a pharmaceutically acceptable salt thereof. The particular interaction that takes place between the two components makes even high concentrations of agarose injectable and tolerable, said high concentrations being particularly useful for ensuring the duration and stability over time of the aesthetic results that are achievable using this filler.

16 Claims, No Drawings

FILLER COMPOSITION FOR THE TREATMENT OF LIPOATROPHY

RELATED APPLICATIONS

This application is a continuation of U.S. patent application Ser. No. 14/782,171, filed Oct. 2, 2015, which is a 35 U.S.C. §371 national phase entry of international application PCT/IB2014/060322, with international filing date Mar. 31, 2014, which claims the benefit of and priority to Italian patent application serial no. MI2013A000507, filed Apr. 4, 2013, the entire contents of each of which are incorporated by reference herein in their entirety.

The present invention refers to a composition comprising agarose and hyaluronic acid, or a pharmaceutically acceptable salt thereof, and that is useful as a filler for the correction of soft tissue volume loss. The composition can be employed for treating lipodystrophy and/or pathological atrophy, or also as a cosmetic agent, for example for the aesthetic treatment of wrinkles.

PRIOR ART

Lipodystrophy is a disease characterised by abnormal conditions of adipose tissue, which causes a redistribution of fat in the human body and a resulting formation of parts having an excess of fats (hypertrophy) and/or parts in which a lack of such substances (atrophy) is observed.

The causes of this anomaly may be of a genetic nature, or induced for example by malnutrition or by the intake of certain drugs, typically antiretroviral drugs for the treatment of HIV infection.

Lipodystrophy mainly affects the cheeks, the cheekbones, the neck and hands, causing precocious aging of the affected areas with consequent damage, mainly aesthetic damage.

The lipostructure technique (or lipofilling) represents the most widely used invasive treatment among the most effective methods currently employed for treatment of this disease. This is a technique that makes it possible to use the body fat of a patient as natural filler material. To ensure long-lasting results, the transplanted fatty material must be capable of surviving in the new environment, without causing adverse effects on the organism.

Moreover, the material must be taken in a manner that is the least traumatic for the patient, utilising for example small syringes with low pressure aspiration. Generally, the adipose material collected initially undergoes purification processes (including centrifugation and similar processes) prior to transplantation. Transplantation takes place by means of the formation of multiple layers, taking special measures that enable the transplanted tissue to take on the structural characteristics of the surrounding tissue.

As an alternative or in addition to the surgical technique described hereinabove, lipodystrophy, especially facial lipodystrophy, can be treated by means of local injections of filler compositions having suitable characteristics and chemical structures. These fillers are capable of ensuring a middle- to long-term, non-permanent duration of results, thus requiring subsequent re-filling treatments. The timing of said re-filling treatments varies mainly depending on the rate of reabsorption of the material utilised and the stability over time of the results achieved.

In this regard, filler compositions that are agarose- and/or hyaluronic acid-based (or in this latter case including the sodium salt thereof) are known in the prior art. However, the concentration of agarose in these compositions must be kept in check and it is usually less than 2%, or in some cases, less than 2.5%. Fillers with higher agarose concentrations would be particularly useful, especially for increasing the stability and duration over time of the results achieved following injection. However, high concentrations of agarose require arduous injection procedures and cause increased rigidity of the composition to be injected. This increased rigidity can, in turn, cause unpleasant sensations for the patient, above all in cases in which the injected areas are sensitive areas such as the lips or cheekbones.

The Applicants have presently found that when agarose is mixed at concentrations comprised between 2.6 and 5% by weight with hyaluronic acid in amounts comprised between 0.1 and 4% by weight, or with a pharmaceutically acceptable salt thereof, the aqueous composition that can be obtained has excellent filler properties, as shall be described in detail herein below.

The present composition can be administered in the deep layer of the skin, functioning as a support for the tissue being treated, resting on suitable tissue, generally bone tissue. Owing to its particular structure and its in vivo behaviour, the present composition reveals a long duration of permanence in the injection site, excellent biocompatibility and it maintains the characteristic softness and elasticity that make it particularly suited to treatment of sensitive areas of the human body, such as the cheekbones and lips for example.

SUMMARY OF THE INVENTION

In a first aspect, the invention refers to a filler composition comprising:
agarose in an amount comprised between 2.6 and 5% by weight;
hyaluronic acid or a pharmaceutically acceptable salt thereof in amounts comprised between 0.1 and 4% by weight, and
water until 100% is reached.

In a further aspect, the invention refers to a process for the preparation of the filler composition cited above, said process comprising:
a) preparing an aqueous solution of agarose and an aqueous solution of hyaluronic acid or a pharmaceutically acceptable salt thereof,
b) bringing the two solutions to a temperature near the gel point,
c) mixing the two solutions specified in step b by homogenisation, and
d) making the resulting composition iso-osmolar with respect to the blood plasma of the subject to be treated, by the addition of salts, preferably alkaline chlorides and/or phosphates.

The composition obtained (or obtainable) by means of the process indicated has an internal structure comprising intersections between molecules of agarose and of the hyaluronic acid component, which make it possible for the composition to be injected and to perform the desired filler function, as described in detail herein below.

In an additional aspect, the invention concerns the present composition for use as a medicament, particularly for the treatment of lipodystrophy, and preferably atrophy.

Lastly, an aspect of the invention is constituted by the use of the present filler composition as a cosmetic agent for the treatment of areas of the human body, preferably the face or hands, affected by skin blemishes, deficits of the dermis of the skin or by volumetric weakening.

DETAILED DESCRIPTION

Unless specified otherwise, "percentage (%) by weight" refers to the weight of the single component with respect to the total weight of the composition.

The term "hyaluronic acid component" is intended to indicate hyaluronic acid and/or a pharmaceutically acceptable salt thereof, preferably sodium salt.

The term alkaline chloride or phosphate is intended as a chloride salt, phosphate or phosphate acid of an alkali metal including for example: sodium, potassium and the like.

Advantageously, owing to its particular concentration of agarose, the present filler composition makes it possible to achieve slow absorption by the human body, which translates into a prolonged permanence time of the filler in the injection site, enabling a reduction or even the elimination of subsequent refilling treatments. In fact, the Applicants have surprisingly found that when agarose is utilised in amounts comprised between 2.6% and 5% by weight, the association with hyaluronic acid, or a pharmaceutically acceptable salt thereof, it causes physical interaction between the two components, which makes it possible to obtain a final composition having a filler effect and a particular in-vivo behaviour In fact, the agarose and the hyaluronic acid component tend to form an intersecting structure, in which they intersect one with the other, which characterises the invention and provides excellent properties in terms of viscosity and injectability. Moreover, in-vivo, the hyaluronic acid is quickly absorbed by the organism and said intersecting structure with the agarose remains. The remaining (agarose) structure thus takes on a physical form that exhibits channels or tunnels (previously occupied by the hyaluronic acid) and differs from the form that the agarose would have if injected alone, without the combination with hyaluronic acid. These channels provide the injected filler with increased elasticity, a high degree of softness and a high level of bioavailability, which are not otherwise achievable by injecting agarose alone at the concentrations indicated.

Furthermore, the present filler composition exhibits slow absorption and offers excellent results in terms of softness and elasticity also when utilised in cosmetic surgery involving the face, or particularly sensitive areas.

In one embodiment, the composition comprises agarose in amounts comprised between 2.6 and 4% by weight, even more preferably between 3 and 3.6% by weight. The agarose is a linear polymer made up of alternating units of D-galactose and 3,6-anhydro-L-galactose linked together by glycosidic bonds. It is commercially available and can be utilised directly without particular procedures, such as purification or similar procedures.

As regards the hyaluronic acid (CAS No. 9004-61-9), it is an unbranched glycosaminoglycan, obtained by condensation of thousands of disaccharide units made up of residues of glucuronic acid and N-acetylglucosamine.

In the present composition, the hyaluronic acid can be present as such and/or in the form of a pharmaceutically acceptable salt, intended as a salt that is suitable for in-vivo administration. In this regard, the preferred pharmaceutically acceptable salts of hyaluronic acid consist of alkali metal salts, sodium hyaluronate (CAS No. 9067-32-7) being particularly preferred.

In any case, the hyaluronic component (acid or salt) is present in amounts that can vary between 0.1 and 4% by weight, preferably comprised between 0.4 and 0.8% by weight.

High concentrations of the hyaluronic component could lead to defective solubilisation, whereas concentrations lower than 0.2% by weight would prove to be of little advantage for the realisation of an efficient intersecting structure with agarose.

It should be emphasised that in the absence of said hyaluronic component, if utilised at the concentrations indicated herein (i.e., 2.6-5%), the agarose alone would be poorly injectable (principally due to the structural rigidity thereof) and poorly tolerable on the part of the subject (principally owing to the rigidity thereof). However, the present composition does permit injection of high concentrations of agarose (even higher than 2.5%), achieving advantageous effects as regards softness, duration over time and biocompatibility compared to known fillers of the prior art.

Moreover, the fact that agarose in-vivo exhibits tunnels or channels can be useful also in terms of serving as a vehicle for other substances such as proteins and amino acids, as described in detail herein below.

In fact, in particular, in addition to the components described above and characterising the invention, the present composition can contain additional compounds, for example to further improve bioavailability and/or to increase in vivo stability over time. In this regard, the composition can also comprise at least one protein and at least one natural amino acid.

The filler composition preferably comprises at least one protein or one amino acid in amounts that can vary from 0.01% to 0.6% by weight, values comprised between 0.02 and 0.15% being particularly preferred.

In one embodiment, the filler composition of the invention comprises the protein resilin, preferably in amounts comprised between 0.01 and 0.1% by weight, even more preferably comprised between 0.01 and 0.04%. The presence of this protein makes it possible to increase the sensitivity of the tissues adjacent to the injection site, ensuring greater in-vivo stability and thus longer duration of the cosmetic and/or therapeutic results achieved.

In an equally preferred embodiment, the composition can contain, in addition to or in place of the protein, at least one natural amino acid. The presence of at least one amino acid compound is useful particularly for increasing the biocompatibility of the injected composition, while also making it possible to reduce undesirable phenomena related to the migration of the filler injected. The composition preferably comprises at least one amino acid selected from among the following:

isoleucine at 0.25% or lower percentages
  leucine at 0.4% or lower percentages
  glycine at 0.4% or lower percentages
  alanine at 0.3% or lower percentages
  valine at 0.25% or lower percentages
  lysine at 0.5% or lower percentages
  serine at 0.35% or lower percentages.

In a further aspect, the present invention refers to a process for the preparation of the filler composition specified herein above, said process comprising:
  a) preparing an aqueous solution of agarose and an aqueous solution of hyaluronic acid or a pharmaceutically acceptable salt thereof,
  b) bringing the two solutions to a temperature near the gel point,
  c) mixing the two solutions specified in step b by homogenisation, and
  d) making the resulting composition iso-osmolar with respect to the blood plasma of the subject to be treated, by the addition of salts, preferably alkaline chlorides and/or phosphates.

The aqueous solutions of agarose and the hyaluronic component specified in step a can be obtained using deionised or distilled water, or preferably water for injection, intended as sterile water, free of bacteria and known in the sector. In a preferred embodiment, said solutions are prepared by means of dissolution of the two components in water at a temperature higher than 50° C., preferably comprised between 70 and 90° C. The concentration of the two solutions obtained preferably ranges between 0.01% and 5%, concentrations of between 0.1 and 4% being particularly preferred.

Once the solutions specified in step a have been obtained, they are cooled to a temperature near the gelling temperature, so as to ensure effective interaction of the two components during the subsequent homogenisation step.

In a preferred embodiment, the two solutions are cooled to a temperature comprised between 30° C. and 50° C., more preferably between 35° C. and 45° C.

Temperatures lower than 30° C. would lead to solidification of the masses, jeopardising the subsequent mixing thereof, whereas temperatures higher than 50° C. would prove to be too distant from the gelling temperature of the solutions.

Cooling of the aqueous solutions of agarose and hyaluronic acid (or salt) according to step b, can take place by means of the use of techniques known to the person skilled in the art, such as a Peltier type of immersion cooler.

Once cooled, the two solutions are mixed together (step c) so as to obtain a homogenous mixture, defined as having a statistically identical composition in every point of the space.

Homogeneity of the mixture is required to enable physical interaction of the two components and to obtain the solid intersecting structure that characterises the present filler composition. Homogenisation takes place using homogenisers known in the art, for example rotary blade mixers, ultrasonic probes or colloid mills.

In a preferred embodiment, said step takes place using an ultrasonic homogeniser, as it makes it possible to achieve excellent results in terms of homogeneity in short periods of time.

Step c generally takes place at a temperature comprised between 20 and 35° C.

Once a homogeneous mixture of the two agarose and hyaluronic components has been obtained, the present process comprises a step for adjusting the osmolarity of said mixture, so as to make the final composition iso-osmolar with respect to the blood plasma of the subject to be treated (step d). This step is particularly important for enabling the composition, when in-vivo, to bond with the tissues adjacent to the injection site, reducing defence and rejection reactions on the part of the human body. Osmolarity is a physical measurement known to the person skilled in the art, measuring the concentration of chemical solutions based on the total number of molecules and ions present in a liter of solution.

The term "iso-osmolar" is intended to indicate the fact that the present composition has substantially the same ion content as the blood plasma.

In this regard, the mixture obtained in step c is supplemented with alkaline salts such as chlorides and/or phosphates, preferably present in aqueous solutions. The concentrations of these aqueous solutions can vary preferably between 0.5 and 0.9% in the case of chloride salt and between 0.1 and 0.4% in the case of phosphate salt.

The chloride is preferably chosen from among: NaCl, KCl, and mixtures thereof, whereas the phosphate preferably consists of sodium phosphate ($Na_3PO_4$) and/or sodium acid phosphate ($NaH_2PO_4$). In one embodiment, an aqueous solution containing 0.6-0.8% NaCl and 0.2-0.4% sodium phosphate by weight is added.

Preferably, a solution known in the art as "phosphate buffered saline" (PBS) is added, this solution being defined as an aqueous saline solution containing given amounts of sodium chloride, sodium phosphate and possibly potassium chloride. Said solution can be prepared (typically when needed) or it can be easily purchased on the market ready for use.

The aqueous solution containing the salts specified above can be added simply by mixing, at a temperature generally comprised between about 15° C. and 35° C.

In one embodiment, the present process also comprises a subsequent step e of crushing the structured gel obtained in step d. The crushing can take place by means of methods known in the sector, which typically involve the use of sieves decreasing in mesh size and the like. In this manner, the resulting composition can be obtained in the form of microgranules, which are particularly suitable in the event that one wishes to utilise injection devices equipped for example with needles of very small diameters.

The present process makes it possible to obtain a final composition comprising agarose (at high concentrations) interconnected with molecules of a hyaluronic component that substantially functions as a glidant. In this regard, it should be mentioned that a composition comprising only agarose in an injectable material would prove to be constituted by strongly solvated agarose cubes, with short and rigid bonds, whereas if only hyaluronic acid or the salts thereof were employed as the sole product, an injectable material that is easily dispersible, and thus quickly reabsorbed, would be obtained. Both situations would result in a filler that is hardly utilisable owing to a level of rigidity that is too high or to a permanence time in the site that is too brief, respectively. However, owing to the physical interaction between the two components according to the present invention, it is possible to obtain a product that comprises agarose in amounts comprised between 2.6% and 5% by weight, and that once injected, is capable of bonding to the surrounding tissues, preventing the undesirable effects of migration or instability.

Furthermore, this structure offers the patient the sensation of softness and comfort, which together with high bioavailability and duration over time makes the composition obtained with the present process particularly useful for the treatment of lipoatrophy or for the correction of blemishes caused by skin atrophy (for example wrinkles) or by volumetric weakening of the skin, also in sensitive areas such as the lips or the cheekbones.

As indicated hereinabove, the present filler can be utilised as a cosmetic agent and as a therapeutic agent. The composition of the invention can be typically administered to a subject or patient by injection directly in the deep layer of the skin, functioning as a support for that same layer, resting on suitable supporting tissue, for example the bone tissue.

By way of example, in the case of filling volumetric deficits caused by facial atrophy in the course of antiretroviral treatment of HIV-positive patients, the filler is injected into the subdermal skin, resting it for example over the surface of the cheekbone. Although it has a high concentration of agarose, the filler can be easily distributed owing to the presence of the hyaluronic component and thus optimise the aesthetic support functions thereof.

Therefore, in another aspect the invention refers to the present composition for use as a medicament, particularly as a filler agent for the treatment of lipodystrophy, preferably atrophy. The composition is preferably suited to use for the treatment of facial lipoatrophy, even more preferably in HIV-positive patients undergoing antiretroviral therapy, which is precisely what is determining alterations in the distribution of the adipose tissue.

In a further aspect, the invention refers to the use of the present composition as a cosmetic filler agent, preferably for the treatment of skin blemishes caused by cutaneous or subcutaneous atrophy, including for example wrinkles or volume loss affecting the soft tissues.

In particular, the present filler is suitable for the treatment of superficial, medium, medium-deep and deep wrinkles, and in general for all aesthetic treatments needed to give the affected area a rejuvenated or improved look. Preferably, the present composition is useful as a filler with a filling effect for increased volume of the cheekbones and lips, or for filling the nasolabial folds or for remodelling of the chin and jawline. The composition can be utilised also as a cosmetic agent for remodelling the hands, or more generally as a cosmetic agent for areas of the human body affected by soft tissue volume loss.

In a further aspect, the present invention also refers to a cosmetic or therapeutic method for the treatment of lipodystrophy, which comprises administering the present filler composition to a patient, preferably in amounts comprised between 0.1 ml and 10 ml. In one embodiment, the method is implemented by means of a series of injections of the composition, which preferably undergoes crushing as indicated hereinabove, so as to form in vivo a multi-layered deposit of the injected composition.

The invention claimed is:

1. A process for preparing a filler composition consisting of agarose in an amount between 2.6% and 5% by weight; hyaluronic acid or a pharmaceutically acceptable salt thereof, in an amount between 0.1 and 4% by weight; water and salt, the process comprising:
    a) preparing an aqueous solution of agarose; and an aqueous solution of hyaluronic acid or a pharmaceutically acceptable salt thereof;
    b) cooling each solution to a temperature near its gel point;
    c) mixing the solutions by homogenization to form a composition; and
    d) adding salt to the homogenized composition, mixing to form an iso-osmolar composition with respect to blood plasma.

2. The process of claim 1, wherein the salt is saline.

3. The process of claim 2, wherein the saline is sterile.

4. The process of claim 1, wherein the hyaluronic acid is non-crosslinked.

5. The process of claim 1, wherein the temperature in the cooling step is between 30° C. and 50° C.

6. The process of claim 1, wherein cooling comprises use of an immersion cooler.

7. The process of claim 1, wherein the agarose is in an amount between 3.0% and 3.6%.

8. The process of claim 1, wherein the composition has an internal structure comprising intersections between agarose molecules and hyaluronic acid.

9. The process of claim 1, wherein mixing comprises use of a rotary blade mixer, an ultrasonic probe, or a colloid mill.

10. The process of claim 1, wherein the mixing step occurs at a temperature between 20° C. and 35° C.

11. The process of claim 1, wherein the salt is phosphate buffered saline solution.

12. The process of claim 1, wherein the salt is selected from alkaline chlorides or phosphates.

13. The process of claim 12, wherein the chlorides are selected from NaCl or KCl, and wherein the phosphates are selected from sodium phosphate or sodium acid phosphate.

14. The process of claim 1, wherein the adding step occurs at a temperature between 15° C. and 35° C.

15. The process of claim 1, wherein the adding step produces a structured gel.

16. The process of claim 1, further comprising the step of crushing the structured gel to obtain microgranules.

* * * * *